(12) United States Patent
Hordos

(10) Patent No.: US 9,944,244 B1
(45) Date of Patent: Apr. 17, 2018

(54) HYBRID INFLATION SYSTEM WITHOUT PYROTECHNIC CHARGE

(71) Applicant: TK Holdings Inc., Auburn Hills, MI (US)

(72) Inventor: Deborah L. Hordos, Troy, MI (US)

(73) Assignee: TK Holdings Inc., Aurburn Hills, MI (US)

( * ) Notice: Subject to any disclaimer, the term of this patent is extended or adjusted under 35 U.S.C. 154(b) by 0 days.

(21) Appl. No.: 15/422,845

(22) Filed: Feb. 2, 2017

Related U.S. Application Data

(63) Continuation of application No. 14/635,774, filed on Mar. 2, 2015, now abandoned.

(60) Provisional application No. 61/946,697, filed on Feb. 28, 2014.

(51) Int. Cl.
| | |
|---|---|
| *B60R 21/0132* | (2006.01) |
| *B60R 21/272* | (2006.01) |
| *C06D 5/02* | (2006.01) |
| *F42B 3/04* | (2006.01) |
| *B60R 21/01* | (2006.01) |

(52) U.S. Cl.
CPC ........ *B60R 21/0132* (2013.01); *B60R 21/272* (2013.01); *C06D 5/02* (2013.01); *F42B 3/04* (2013.01); *B60R 2021/01211* (2013.01); *B60R 2021/01272* (2013.01)

(58) Field of Classification Search
CPC .......... F42B 3/04; F42B 3/045; B60R 21/264; B60R 21/268; B60R 21/272; C06D 5/00; C06D 5/02
USPC ................. 102/530, 531; 280/736, 737, 741
See application file for complete search history.

(56) References Cited

U.S. PATENT DOCUMENTS 9,321,426 B1 * 4/2016 Krupp .................. B60R 21/264

* cited by examiner

Primary Examiner — Bret Hayes
(74) Attorney, Agent, or Firm — Meunier Carlin & Curfman LLC

(57) ABSTRACT

A gas generator includes a supply of stored gas containing carbon dioxide, and a magnesium supply or source, such as magnesium mesh, that is readily ignitable in the presence of carbon dioxide in the presence of heat.

20 Claims, 5 Drawing Sheets

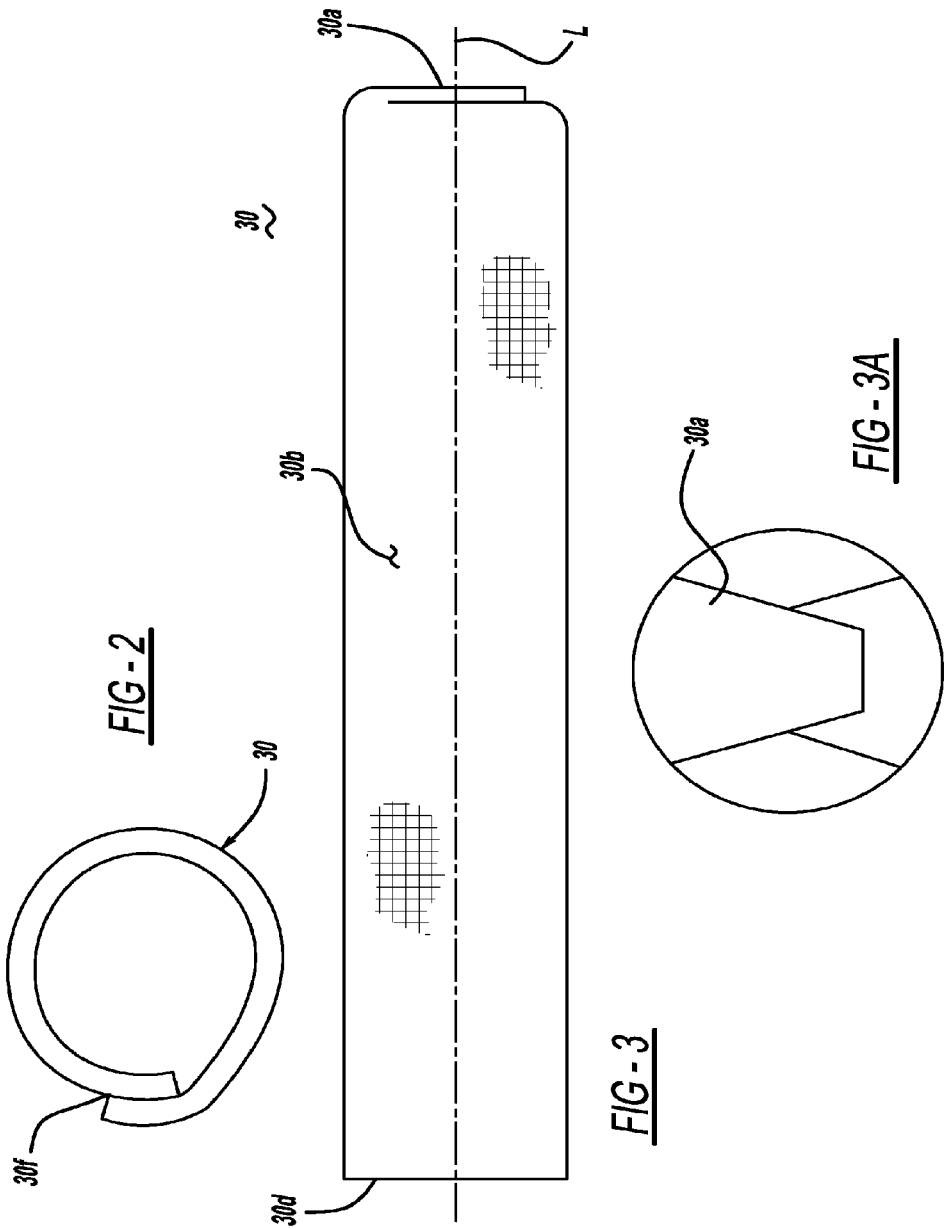

HYBRID INFLATION SYSTEM WITHOUT PYROTECHNIC CHARGE

CROSS REFERENCE TO RELATED APPLICATIONS

This application is a continuation of U.S. patent application Ser. No. 14/635,774, filed Mar. 2, 2015, which claims priority to U.S. Provisional Application Ser. No. 61/946,697, filed Feb. 28, 2014, the disclosure of which is incorporated herein by reference.

BACKGROUND OF THE INVENTION

The present invention relates to gas generating systems and, more particularly, to a container for holding and positioning a gas generant material incorporated into a hybrid gas generating system. Alternatively, the hybrid gas generator may contain a magnesium mesh in the presence of carbon dioxide, that in the presence of heat burns to provide heat and combustion products in lieu of a standard pyrotechnic charge.

In the field of gas generating systems, there is an ongoing need to reduce the number of system components, the cost of each component, the weight of each component, and the complexity of the system from a manufacturing perspective.

SUMMARY OF THE INVENTION

In one aspect of the embodiments of the present invention, a gas generant container assembly comprises a porous container defining a chamber therein, and a porous separator positionable and securable within the chamber so as to divide the chamber into at least a pair of sub-chambers.

In another aspect of the embodiments of the present invention, a porous gas generant container comprises a closed base portion, and at least one wall formed integrally with the base portion and extending from the base portion to define a chamber and an opening providing access to the chamber.

In another aspect of the embodiments of the present invention, a sub-assembly for use in a gas generating system includes a porous gas generant container having a closed base portion and a wall extending from the base portion to define a chamber, and a porous separator positioned within the chamber so as to divide the chamber into at least a pair of sub-chambers. A gas generant material is positioned within a sub-chamber of the pair of sub-chambers. The separator is adjustably securable within the chamber to abut the gas generant material to urge the gas generant material against the base portion. In accordance with the present invention, the container may contain magnesium that burns in the presence of a stored gas such as carbon dioxide.

Alternatively, the hybrid gas generator may contain a magnesium source such as magnesium chips or mesh in the presence of carbon dioxide, that when exposed to heat from an igniter burns to provide heat and combustion products in lieu of a standard pyrotechnic charge. Further, the hybrid gas generator may contain an igniter for actuating combustion of the magnesium source and the carbon dioxide, and may specifically omit any gas generating composition within the gas generator, in accordance with the present invention.

BRIEF DESCRIPTION OF THE DRAWINGS

In the drawings illustrating embodiments of the present invention:

FIG. 2 is an end view of a gas generant container in accordance with an embodiment of the present invention.

FIG. 3 and FIG. 3A are a side view of the gas generant container shown in FIG. 2

DETAILED DESCRIPTION

Figure 1:
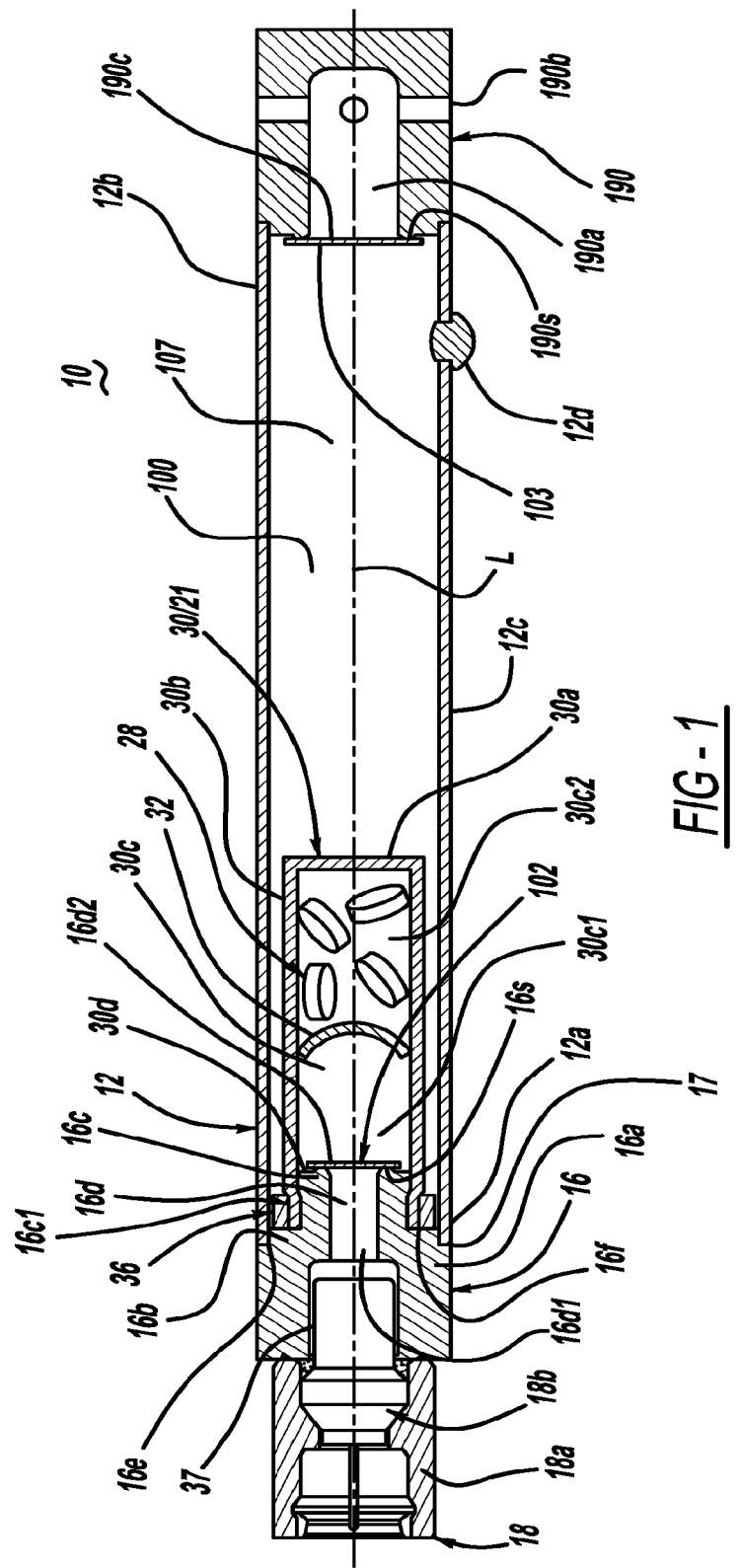
FIG. 1 is a cross-sectional side view of a gas generating system incorporating a gas generant container in accordance with an embodiment of the present invention.

Referring to FIG. 1, one embodiment of a gas generating system 10 includes a substantially cylindrical housing 12 having a first end 12a, a second end 12b opposite the first end, and a wall 12c extending between the ends to define a housing interior cavity 100. Housing 12 is made from a metal, metal alloy, or other suitable material and may be a cast, stamped, deep-drawn, extruded, or otherwise formed.

Wall 12c may have a fill hole 12d formed therein to enable filling of housing cavity 100 with a compressed gas, in a manner known in the art. Fill hole 12d is then sealed in a manner known in the art using, for example, a plug of a suitable sealing material positioned in the opening to trap the compressed gas within housing 12 after filling.

In the exemplary embodiment shown in FIG. 1, a first end closure 16 includes a base portion 16a, a first portion 16b projecting from base portion 16a, and a second portion 16c projecting from first portion 16b. Base portion 16a and first portion 16b combine to define a generally annular first shoulder 16e which may abut housing first end 12a when the first end closure 16 is secured to the housing, thereby forming a seam 17 between housing first end 12a and first end closure 16. First end closure 16 is welded or otherwise suitably secured to housing first end 12a along the seam 17 or along a suitable interface formed between first end closure 16 and housing first end 12a. Housing first end 12a may also slidingly engage an outer surface of first portion 16b to aid in centering and/or positioning the end closure 16 with respect to the housing.

First portion 16b and second portion 16c combine to define a generally annular second shoulder 16f which may abut a gas generant container 30 (described below) when the container 30 is secured to the first end closure 16 as described below. Container 30 may also slidingly engage an outer surface 16c1 of second portion 16c when the container is applied to first end closure 16. First end closure 16 also includes a passage 16d formed therein. Opening 16d has a first end 16d1 and a second end 16d2 and is configured to enable fluid communication between an initiator 18b (described below) extending into (or in fluid communication with) first end 16d1 and housing interior cavity 100 after activation of the gas generating system. First end closure 16 is made from a metal, metal alloy, or other suitable material and may be a cast, stamped, machined or otherwise suitably formed.

In the embodiment shown in FIG. 1, an initiator assembly 18 is welded or otherwise suitably secured to first end closure 16. In the embodiment shown, initiator assembly 18 includes a shell 18a and an initiator 18b crimped or otherwise secured to the shell such that initiator 18b projects from the shell for insertion into cavity 37 of first end closure 16.

A rear portion of shell 18a may be configured to provide an interface mateable with a complementary connector (not shown) of a wiring harness or other suitable initiator activation signal transmission medium (not shown). The attachment between shell 18a and first end closure 16 forms a substantially gas-tight seal at the contact interface between the shell and the end closure, to prevent escape of generated gases along the interface. Shell 18a may be formed from a metal or metal alloy using a suitable manufacturing process, such as casting or machining. Alternatively, shell 18a may be formed from a moldable material, for example, a castable metal alloy, or a suitable polymer. Initiator 18b may be formed as known in the art. One exemplary igniter construction is described in U.S. Pat. No. 6,009,809, which is incorporated herein by reference. An o-ring seal or other suitable seal (not shown) may be positioned along an interface between the initiator 18b and the shell 18a to form a substantially gas-tight seal between the initiator and the shell.

Referring to FIGS. 1-3, a gas generant container 30 may be provided for containing and positioning a gas generant material 28 within housing 12. In the exemplary embodiment shown in FIGS. 1-3, container 30 is an elongated, generally tubular basket. Container 30 includes a base portion 30a, at least one wall 30b extending from the base portion to define a chamber 30c into which the a gas generant material 28 may be is-positioned, and an opening (in the embodiment shown in FIG. 1, an open end 30d opposite base 30a) which provides access to chamber 30c. In the embodiment shown in FIG. 1, container 30 extends into (and along a portion of the extent of) cavity 100. Thus, a gas generant material 28 positioned in container 30 fluidly communicates with and is exposed to the compressed gas 107 stored in cavity 100 prior to activation of the gas generating system. Container 30 positions and maintains the gas generant material 28 in a predetermined region within the housing before and during combustion of the gas generant. The container also acts as a filter for filtering particulates from gas generant combustion products, and as containment for the separator 32 (described below) and for fragments (if any) resulting from activation of initiator 18b and/or from rupture of seal 102 (described below), thereby preventing such materials from entering and/or obstructing the gas flow through and out of the gas generating system.

In accordance with the present invention, the container 30 may be formed from any of a variety of porous base materials (for example, a metallic mesh, perforated/expanded metal sheet, or a compressed knitted metal wire) known in the art and suitable for filtering gas generant combustion products and for the other container functions described herein. In particular, the container 30 may contain magnesium as stated herein, thereby providing a combustible magnesium source 21 in accordance with the present invention. Suitable metallic mesh is readily obtainable from suppliers such as Wayne Wire, Inc., of Kalkaska, Mich. Suitable compressed knitted metal wire is commercially available from vendors such as Metex Corp. of Edison, N.J. The container base material may also be specified so as to have a degree of stretchability and/or resilience, to aid in cushioning against shock and/or vibration any gas generant impacting the walls and/or base portion of the container. An element described herein as being formed from a "porous" base material is understood to be formed from a base material that is permeable by a fluid, such as pressurized gas. In the embodiment shown in FIG. 1, wall 30b is formed integrally with the base portion 30a (i.e., wall 30b is formed as a single piece with base portion 30a).

The container 30 may be formed in any desired length or shape according to the requirements of a particular application. For example, the configuration of the container may be configured to conform to the interior volume of the portion of the gas generating system in which the container resides. Similarly, the container may be sized to accommodate a desired quantity and/or configuration of gas generant material.

In one embodiment, the container is fabricated by forming the base material into a cylinder and closing one end of the cylinder to form the base portion 30a. Material of the cylinder may overlap longitudinally as shown in FIG. 2 to form a longitudinal seam 30f. The base portion end 30a may be closed by, for example, folding over and/or overlapping portions of the material. The closed end and seam 30f may then be sealed using welding or any other suitable sealing method(s). In other embodiments, the container may be in the form of a sock or closed sleeve shape knitted from a suitable material. Other methods may also be used to form the container.

Referring again to FIG. 1, gas generant material 28 is positioned within container chamber 30c. In one embodiment, the gas generant blocks comprise a high gas-yield, low solids-producing gas generant composition, such as a "smokeless" gas generant composition. Such gas generant compositions are exemplified by, but not limited to, compositions and processes described in U.S. Pat. Nos. 6,210,505, and 5,872,329, each incorporated by reference herein. As used herein, the term "smokeless" should be generally understood to mean such propellants as are capable of combustion yielding within a range of about 60% to about 80% gaseous products, based on a total product mass; and, as a corollary, no more than about 15% solid products and, preferably, about 10% solid products, based on a total product mass. U.S. Pat. No. 6,210,505 discloses various high nitrogen nonazide gas compositions comprising a non-metal salt of triazole or tetrazole fuel, phase stabilized ammonium nitrate (PSAN) as a primary oxidizer, a metallic second oxidizer, and an inert component such as clay or mica. U.S. Pat. No. 5,872,329 discloses various high nitrogen nonazide gas compositions comprising an amine salt of triazole or tetrazole fuel, and phase stabilized ammonium nitrate (PSAN) as an oxidizer. Other types of gas generant materials may also be used, according to the requirements of a particular application. For example, U.S. Pat. No. 5,035,757, herein incorporated by reference in its entirety, as are all other patents described herein, exemplifies yet other gas generating compositions that may also be used in the present gas generator. The gas generant may be in any suitable form, for example, tablets, granules, wafers, an extruded body, or any other form depending on the requirements of a particular application.

Optionally, a gas generant container assembly may be formed by inserting a screen separator 32 into container chamber 30c to aid in confining the gas generant material 28 within a predetermined portion of the chamber. Separator 32 is adjustably securable to a portion of the container to enable the position of the separator within the container to be adjusted to at a desired location within the container and then secured or fixed in the desired position. In one embodiment, separator 32 is in the form of a disc which is pressed into the chamber 30c, slidingly engaging container wall 30b in an interference fit until positioned as desired within the chamber. The interference fit then maintains the screen separator in the desired position prior to activation of the gas generating system. The separator may be inserted into the chamber to a position where it abuts the gas generant material when the desired amount and/or configuration of gas generant material is inserted into the container, to aid in immobilizing the gas generant. This aids in preventing breakage of the gas generant due to impact and vibration. The material and/or configuration of the separator may also be specified such that the body of the separator (or at least the portion of the body inside the edges of the separator) is relatively resilient, thereby enabling the disc to provide a degree of cushioning against shock and/or vibration to any gas generant material impacting the separator. As the separator may be positioned and secured at any desired position within the chamber, the amount of gas generant positioned within the chamber may be varied according to the requirements of a particular application. When positioned inside chamber 30c, the separator 32 is positioned along a longitudinal axis L of the container and separates the chamber 30c into a pair of longitudinally adjacent compartments or sub-chambers 30c1 and 30c2, one of which (30c1) is relatively closer to end closure passage second end 16d2, and one of which (30c2) is relatively farther away from end closure passage second end 16d2 than is sub-chamber 30c1. In the embodiment shown in FIGS. 1 and 2, gas generant 28 resides in sub-chamber 30c2.

Screen separator 32 may be formed from any of a variety of materials (for example, a carbon fiber or metallic mesh, perforated/expanded metal sheet, or a compressed knitted metal wire) known in the art. Suitable metallic mesh is readily obtainable from suppliers such as Wayne Wire, Inc., of Kalkaska, Mich. Suitable compressed knitted metal wire is commercially available from vendors such as Metex Corp. of Edison, N.J. The separator 32 may, in accordance with the present invention, be formed from or contain magnesium.

Although the separator material shown in FIG. 1 is in the form of a disc, a separator 32 suitable for cushioning and/or screening the gas generant and suitable for positioning within chamber 30c may have any of a wide variety of alternative forms. In another alternative embodiment, the disc or other screening structure is positioned within chamber 30c and attached to wall 30b by crimping or other suitable means. Other methods of securing the separator 32 to the container at a desired position within the container interior are also contemplated.

Figure 5:
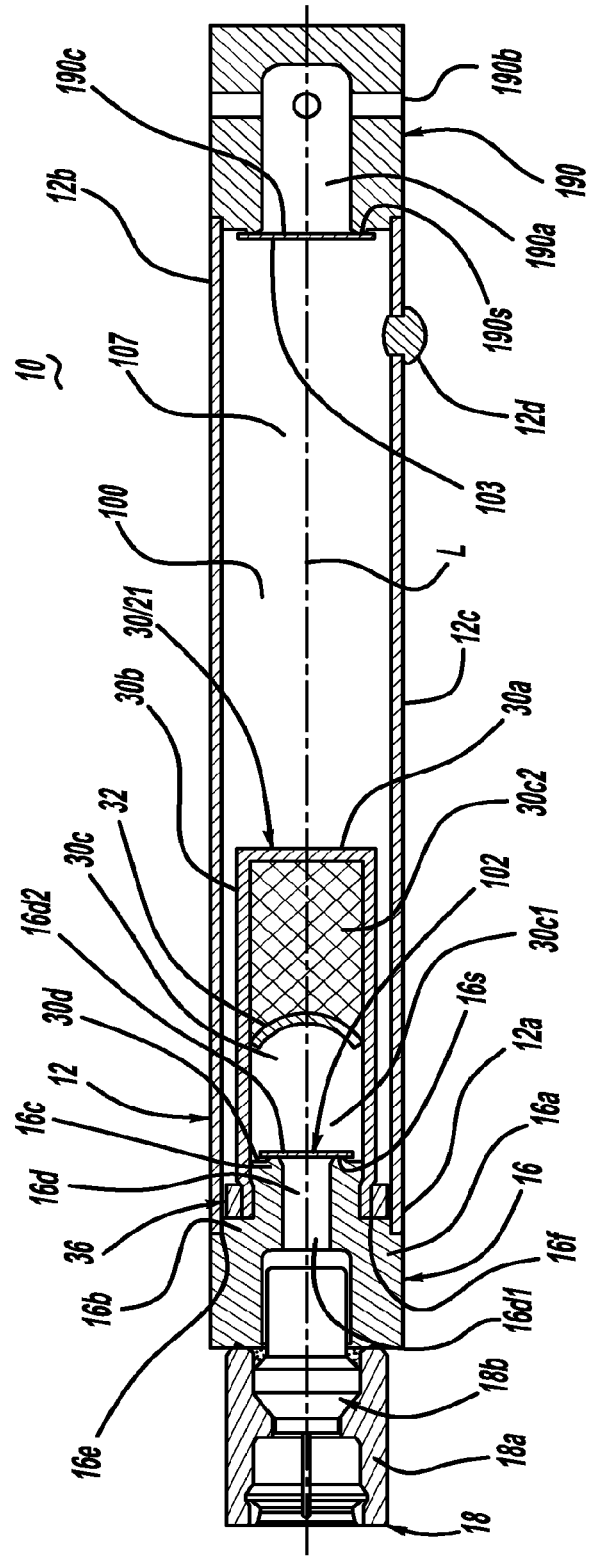
FIG. 5 is a cross-sectional side view of a gas generating system incorporating a gas generant container in accordance with an embodiment of the present invention, wherein no pyrotechnic charge is employed within the stored gas chamber.
Figure 6:
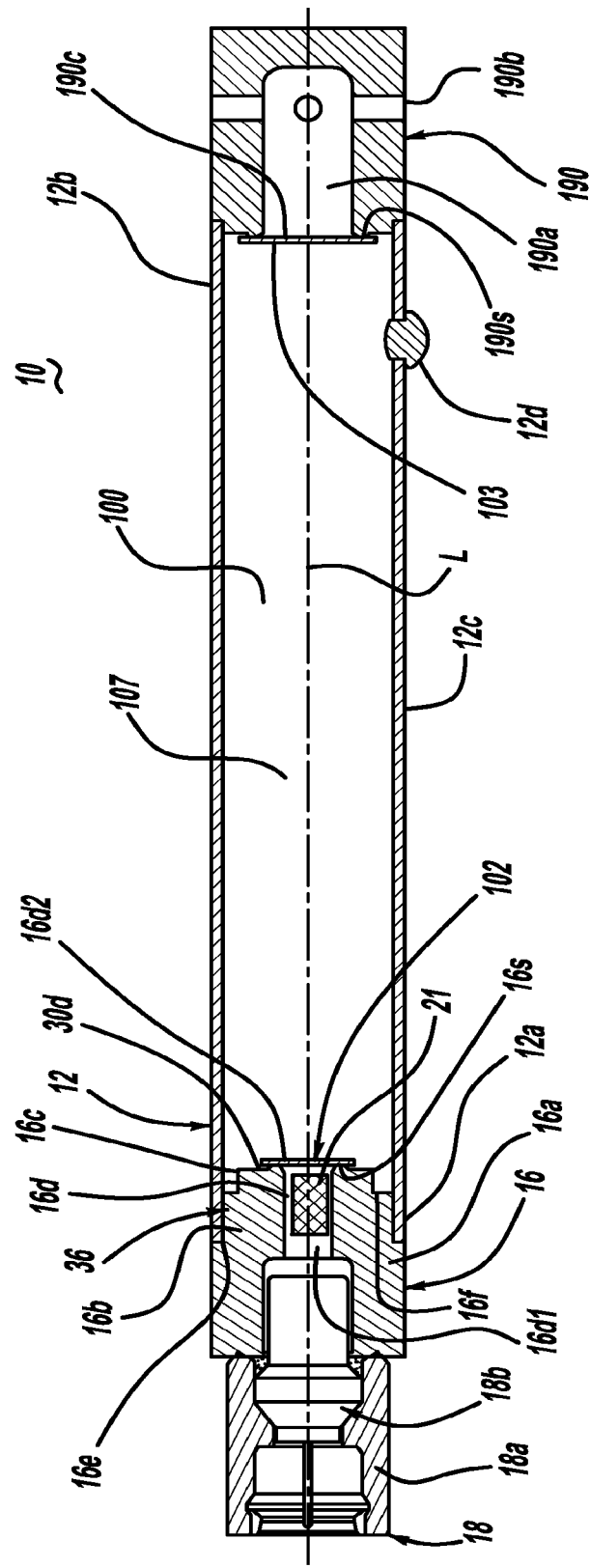
FIG. 6 is a cross-sectional side view of a gas generating system incorporating a magnesium source contained within a sealed ignition chamber.

Using the various elements described herein, a sub-assembly for a gas generating system may be formed including a magnesium-containing gas generant container assembly having a porous container defining a chamber therein, a porous separator positionable and securable within the chamber so as to divide the chamber into at least a pair of sub-chambers, and a gas generant material 28 positioned in a sub-chamber of the pair of sub-chambers. Alternatively, as described herein and as shown in FIGS. 5 and 6, the container 30 may contain only magnesium, whereby the inflator or gas generator 10 is absent any gas generating composition. Accordingly, the magnesium or magnesium source 21 thereby fluidly communicates with the stored pressurized carbon dioxide gas 107 within chamber 100 as it resides within or as part of container 30.

In addition, using the various elements described herein, another sub-assembly for a gas generating system may be formed including an end closure configured for coupling to a portion of a gas generating system, and a sub-assembly as described in the previous paragraph.

Referring again to FIG. 1, a quantity of a known or suitable ignition or booster compound (not shown), may be positioned within housing 12 so as to enable fluid communication between the booster material and any associated gas generant material 28 upon activation of the gas generating system. In one embodiment, the booster material may be positioned in either (or both of) sub-chambers 30c1 and 30c2. If desired for a particular application, a quantity of the booster material may be also (or alternatively) positioned within passage 16d of end closure 16. Combustion of the booster material results in combustion of the gas generant, in a manner known in the art.

A quantity of a known heat-activated auto-ignition material (not shown) may be positioned within the gas generating system so as to enable fluid communication between the auto-ignition material and any associated gas generant material and/or any associated booster material upon activation of the gas generating system. The auto ignition material (not shown) may be placed in housing 12 in proximity to the booster material (if any) and positioned in housing 12 so as to enable thermal communication with the housing, thereby enabling heat transfer from an exterior of the housing to the auto ignition material using the housing as a heat transfer medium. Alternatively, the auto ignition material may be positioned in housing 12 so as to enable heat transfer from the exterior of the housing to the auto ignition material using a heat-transfer medium other than the housing.

The auto-ignition material is a pyrotechnic material which is ignited by exposure to a temperature lower than the ignition temperature of the associated gas generant. As is known in the art, the auto-ignition material is ignited by heat transmitted from an exterior of the system housing to the interior of the housing due to an elevated external temperature condition (produced, for example, by a fire). Combustion of the auto-ignition material results in combustion of the associated gas generant, either directly or through intervening combustion of a booster material. Suitable auto ignition materials are known to those skilled in the art. Examples of suitable auto-ignition materials are nitro-cellulose based compositions and gun powder.

Container 30 may be secured to first end closure 16 using any suitable method. In the embodiment shown in FIG. 1, the container is secured to the first end closure using a crimp ring 36 which is applied over the end portion of the container residing along end closure first portion 16b. The end portion of the container slides over the end closure first portion 16b, and the crimp ring is applied over the container end portion to secure the container end portion on the end closure first portion 16b. Other mechanisms for securing the container end portion along the end closure are also contemplated. For example, the container end portion may be welded or crimped to a portion of the first end closure. Any method(s) used to secure container 30 to first end closure 16 should ensure that the base material of the container will rupture or otherwise fail prior to failure of the attachment of the container to the end closure.

Optionally, a rupturable, fluid-tight seal 102 may be positioned to cover first end closure passage 16d at second end 16d2. Seal 102 retains the stored gas within cavity 100 prior to activation of the gas generating system and rupture of the seal. In the embodiment shown in FIG. 1, the seal 102 extends between and is secured to a shoulder (or shoulders) 16s formed along first end closure 16; however, the seal 102 may be mounted to any suitable surface or surfaces. Various known disks, foils, films, tapes, or other suitable materials may be used to form the seal.

A second end closure 190 is positioned and secured at housing second end 12b. End closure 190 has a first gas receiving passage 190a formed therein. An opening 190c formed in end closure 190 enables fluid communication between housing cavity 100 and first gas receiving passage 190a. One or more gas exit orifices 190b enable fluid communication between passage 190a and an exterior of the end closure. Gases exiting the end closure through orifices 190b may enter an associated gas-actuatable device (not shown) operatively coupled to the gas generating system 10.

In the embodiments shown in FIG. 1, end closure 190 is formed separately from housing 12 and may be attached to housing second end 12b by welding, adhesive attachment, threaded engagement, or any other suitable means, depending on the materials from which the housing and end closure are formed, the operational requirements of a particular application, and other pertinent factors.

The end closure 190 is attached to housing 12 so as to form a substantially gas-tight seal between the end closure and the housing. End closure 190 may be forged, machined, molded or otherwise formed from a metallic material, a polymer material, or any other suitable material depending on the requirements of a particular application. Orifice(s) 190b may be drilled, punched, molded into the part, or otherwise suitably formed.

A rupturable, fluid-tight seal 103 may be positioned over opening 190c to provide a substantially gas-tight seal between cavity 100 and first gas receiving passage 190a. Seal 103 retains the stored gas within cavity 100 prior to activation of the gas source and rupture of the seal. In the embodiment shown in FIG. 1, the seal 103 extends between and is secured to a shoulder (or shoulders) 190s formed along end closure 190; however, the seal 103 may be mounted to any suitable surface or surfaces. Various known disks, foils, films, tapes, or other suitable materials may be used to form the seal.

During assembly of the gas generating system, the gas generant material 28 is positioned within the container. The separator, screen disc, or other gas generant securement mechanism 32 (if employed) may then be positioned to secure the gas generant 28 within a predetermine portion of the container chamber 30c. The initiator assembly 18 and first seal 102 may be secured to first end closure 16. Then the container 30 is then secured to the first end closure 16. The housing 12 is then secured to the first end closure 16. Seal 103 may be applied to the second end closure 190 and the second end closure secured to housing second end 12b.

Operation of the embodiment of the gas generating system shown in FIGS. 1-3 will now be discussed.

Upon receipt of a signal from a crash sensor, an electrical activation signal is sent to initiator 18b. Ignition products resulting from activation of the initiator rupture seal 102 and flow into container chamber 30c to initiate combustion of any booster material and/or gas generant material 28. Furthermore, actuation of igniter or initiator 18b may additionally create a shock wave which propagates through the stored gases in the interior of housing 12 to rupture the exit seal 190C. Alternatively, or in conjunction with the aforementioned shock wave, the initiator may ignite the magnesium and/or propellant within the stored gas, which subsequently creates a pressure increase thereby rupturing the exit seal 190c. Combustion of the gas generant also produces additional gases, which increase the pressure within housing 12. These factors result in rupture of the seal 103 covering second end closure opening 190c. The products of combustion of the gas generant 28 and the gas stored in chamber 100 flow out of the housing through second end closure 190 and out of the second end closure into an associated gas-actuatable device such as an airbag (not shown).

Figure 4:
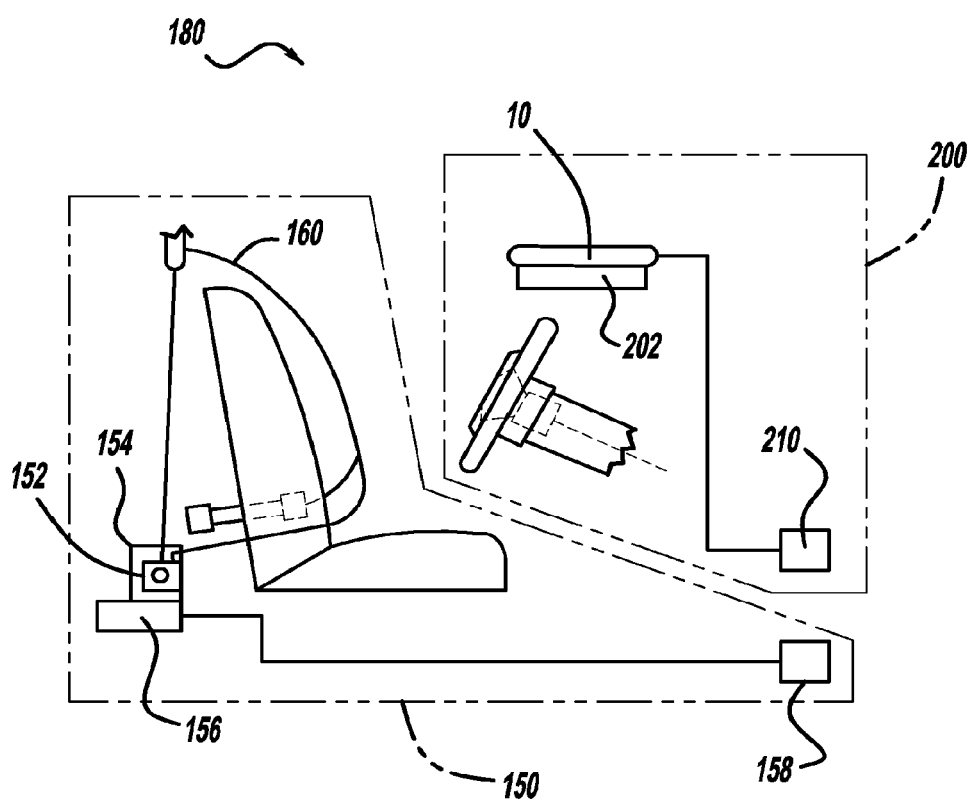
FIG. 4 is a schematic representation of an exemplary vehicle occupant protection system incorporating a gas generating system including a gas generant container in accordance with an embodiment of the present invention.

Referring now to FIG. 4, any of the gas generating system embodiments described herein may be incorporated into an airbag system 200. Airbag system 200 includes at least one airbag 202 and a gas generating system 10 as described herein coupled to airbag 202 so as to enable fluid communication with an interior of the airbag. Airbag system 200 may also be in communication with a crash event sensor 210 operating in association with a known crash sensor algorithm that signals actuation of airbag system 200 via, for example, activation of airbag gas generating system 10 in the event of a collision.

Referring again to FIG. 4, airbag system 200 may also be incorporated into a broader, more comprehensive vehicle occupant restraint system 180 including additional elements such as a safety belt assembly 150. FIG. 4 shows a schematic diagram of one exemplary embodiment of such a restraint system. Safety belt assembly 150 includes a safety belt housing 152 and a safety belt 160 extending from housing 152. A safety belt retractor mechanism 154 (for example, a spring-loaded mechanism) may be coupled to an end portion of the belt. In addition, a safety belt pretensioner 156 may be coupled to belt retractor mechanism 154 to actuate the retractor mechanism in the event of a collision. Typical seat belt retractor mechanisms which may be used in conjunction with the safety belt embodiments of the present invention are described in U.S. Pat. Nos. 5,743,480, 5,553,803, 5,667,161, 5,451,008, 4,558,832 and 4,597,546, incorporated herein by reference. Illustrative examples of suitable pretensioners are described in U.S. Pat. Nos. 6,505,790 and 6,419,177, incorporated herein by reference.

Safety belt system 150 may also be in communication with a crash event sensor 158 (for example, an inertia sensor or an accelerometer) operating in association with a known crash sensor algorithm that signals actuation of belt pretensioner 156 via, for example, activation of a pyrotechnic igniter (not shown) incorporated into the pretensioner. U.S. Pat. Nos. 6,505,790 and 6,419,177, previously incorporated herein by reference, provide illustrative examples of pretensioners actuated in such a manner.

In yet another aspect of the invention shown in FIG. 5, the container 30 described above is in this embodiment may be formed from a magnesium mesh provided again by known metallic mesh suppliers. Accordingly, the container 30 is formed from magnesium mesh or perhaps simply contains magnesium chips (e.g. contained within the container 30) thereby obviating the need of a pyrotechnic material as described in other embodiments herein. As such, in this embodiment, there is no pyrotechnic charge employed in the container 30 because the container 30 is itself the combustible element with the hybrid inflator/system. Instead of ignition of the pyrotechnic charge described above, magnesium would be ignited upon actuation of the inflator and initiator. Heat and combustion products resulting from actuation of the igniter/initiator would then catalyze the combustion of magnesium in the presence of carbon dioxide. Accordingly, the stored gas contains carbon dioxide. In an alternative embodiment, the stored gas may contain a mixture of carbon dioxide and another inert gas, such as carbon dioxide and argon. For example, the stored gas may contains a mixture of carbon dioxide and argon. In accordance with the present invention, magnesium in the presence of carbon dioxide burns with a heat of reaction (about −811 KJ/mol) very similar to methane (about −818 KJ/mol). It will be appreciated that the amounts of gas desired, along with the amounts of magnesium combined with desired or stoichiometric amounts of carbon dioxide may be iteratively determined based on desired design criteria such as total moles of gas desired at the output of the inflator, total heat of combustion, etc.

In further accordance with the present invention, the container 30 may be formed from magnesium, or a magnesium-containing alloy. Further, the chamber 100 may be filled with a pressurized source of carbon dioxide 107. Upon actuation of igniter 18b, the magnesium is heated to combustion, whereby ignition products such as heat, flame, and/or gas contact the magnesium-containing container 30 to result in expansion of the carbon dioxide gases as the magnesium begins to burn. It is alternatively believed that the magnesium may also react with the carbon dioxide in a known manner, thereby forming a combustible system of magnesium and carbon dioxide. The resultant heated and pressurized gases are then released at a predetermined pressure from nozzle 190 through nozzle orifices 190b.

As shown in FIG. 1, and as explained above, the container 30 may if desired contain a gas generating composition 32. Accordingly, a pyrotechnic or gas generating composition as known in the art may be combined with the magnesium mesh within container 30 to enhance the amount of gas produced once the magnesium and stored/pressurized carbon dioxide begin to combust, as gas generating composition 32 combusts.

Alternatively, as stated above, and as shown in FIG. 5, the chamber 100 may if desired contain only carbon dioxide and the magnesium mesh, either as part of the container 30, or as contained within the container 30. Upon actuation of igniter 18b, the magnesium is heated to combustion, whereby ignition products such as heat, flame, and/or gas contact the magnesium-containing container 30 to result in expansion of the carbon dioxide gases as the magnesium begins to burn.

Alternatively, as shown in FIG. 6, the chamber 100 may if desired contain stored gas 107 that is substantially or completely carbon dioxide. A predetermined amount of magnesium 21 (e.g. mesh) may be contained in a cavity 19 proximate to igniter 18b. As the igniter 18b is actuated, resultant ignition products burst seal 102 and concurrently ignite magnesium 21, thereby reacting with and/or expanding the carbon dioxide as combustion of the magnesium is propagated by ignition products from igniter 18b.

It will be understood that the foregoing description of the present invention is for illustrative purposes only, and that the various structural and operational features herein disclosed are susceptible to a number of modifications, none of which departs from the spirit and scope of the present invention. The preceding description, therefore, is not meant to limit the scope of the invention except where specifically indicated. In sum, the scope of the invention should be determined by the scope of the claims as appended hereto.

What is claimed is:
1. A gas generator comprising:
a housing containing pressurized carbon dioxide; and
a porous container contained within said housing and said carbon dioxide and defining a chamber therein, said porous container comprising an ignitable magnesium source.

2. The gas generator of claim 1, wherein said housing contains pressurized carbon dioxide and at least one other gas.

3. The gas generator of claim 1, wherein said magnesium source and said carbon dioxide are in fluid communication prior to actuation of said gas generator.

4. The gas generator of claim 1, further comprising:
an ignition assembly comprising an igniter and an ignition chamber proximate to said igniter,
wherein said magnesium source is stored within said ignition chamber prior to combustion thereof.

5. The gas generator of claim 1, wherein said magnesium source is not contained within said carbon dioxide prior to ignition of said magnesium source.

6. The gas generator of claim 1, wherein said porous container contains a gas generating composition.

7. The gas generator of claim 1 containing no gas generating composition.

8. The gas generator of claim 1, wherein said porous container is formed from a material comprising magnesium.

9. A gas generator comprising:
a first container comprising pressurized carbon dioxide; and
an ignitable magnesium source contained within said first container,
wherein said magnesium source is in fluid communication with said carbon dioxide prior to actuation of said gas generator.

10. The gas generator of claim 9, comprising a second container comprising said magnesium source.

11. The gas generator of claim 9, comprising a second container contained within said first container, said second container comprising magnesium chips.

12. The gas generator of claim 10 further comprising a gas generating composition contained within said container.

13. The gas generator of claim 9 containing no gas generating composition.

14. A gas generator comprising,
a) a housing containing a compressed gas, and
b) an ignitable magnesium source,
wherein the compressed gas consists essentially of a gas selected from the group consisting essentially of carbon dioxide, and mixtures of carbon dioxide and inert gas.

15. The generator of claim 14, containing no gas generating composition.

16. The gas generator of claim 14, wherein the ignitable magnesium source is stored in an ignition assembly comprising an ignitor and an ignition chamber proximate to said ignitor.

17. The gas generator of claim 16, wherein the ignition chamber comprises a rupturable, fluid-tight seal.

18. The gas generator of claim 14, wherein the compressed gas and ignitable magnesium source are not in fluid communication prior to the actuation of the ignitor.

19. The generator of claim 14, further comprising a gas generating composition.

20. The gas generator of claim 14, wherein said magnesium source is in fluid communication with said carbon dioxide prior to actuation of said gas generator.

* * * * *